US008628728B2

(12) United States Patent
Kane et al.

(10) Patent No.: US 8,628,728 B2
(45) Date of Patent: Jan. 14, 2014

(54) NON-INVASIVE COLORIMETRIC-BASED INFECTION DETECTOR AND INFECTION DETECTING BANDAGE

(75) Inventors: James A Kane, Needham Heights, MA (US); Melissa Ricci, Needham Heights, MA (US); Ranganathan Shashidhar, Needham Heights, MA (US)

(73) Assignee: Polestar Technologies, Inc., Needham Heights, MA (US)

( * ) Notice: Subject to any disclaimer, the term of this patent is extended or adjusted under 35 U.S.C. 154(b) by 968 days.

(21) Appl. No.: 12/354,708

(22) Filed: Jan. 15, 2009

(65) Prior Publication Data

US 2010/0178203 A1   Jul. 15, 2010

(51) Int. Cl.
*G01N 33/00* (2006.01)
(52) U.S. Cl.
USPC ............ 422/402; 422/401; 422/68.1; 422/70
(58) Field of Classification Search
USPC .................................. 422/402, 401, 68.1, 70
See application file for complete search history.

(56) References Cited

U.S. PATENT DOCUMENTS 6,391,626 B1 * 5/2002 Adams et al. .............. 435/287.9
2005/0182443 A1 * 8/2005 Jonn et al. ..................... 606/213

* cited by examiner

*Primary Examiner* — Sam P Siefke
(74) *Attorney, Agent, or Firm* — Burns & Levinson LLP; Orlando Lopez

(57) ABSTRACT

A non-invasive, calorimetric infection detector is provided, comprised of a substrate, and one or more indicator compositions disposed upon or incorporated therein. These indicator compositions exhibit a persistent change color when exposed to gaseous oxides of nitrogen and acids formed therefrom, providing a means of detecting NO production in a wound, which has been found to occur at a high level at the onset of infection in a wound. In addition, a bandage is provided, comprised of the detector, as well as a porous portion, and preferably a hydrophobic barrier layer to protect the detector from contamination by water and other fluids draining from the wound. The non-invasive, calorimetric infection detector, and bandage containing same, can be utilized to provide a convenient, easily utilized colorimetric means of detecting the onset of wound infection, thereby enabling caregivers to effectively and timely treat infections.

22 Claims, 2 Drawing Sheets

NON-INVASIVE COLORIMETRIC-BASED INFECTION DETECTOR AND INFECTION DETECTING BANDAGE

FIELD OF THE INVENTION

The present invention provides a non-invasive, colorimetric infection detector capable of detecting the onset of infection in a wound via the detection of nitric oxide (NO) production therein. More particularly, the present invention provides a non-invasive, calorimetric infection detector, which exhibits a persistent color change upon exposure to nitric acid produced by the reaction of NO vapor emitted from a wound upon the onset of infection therein with water and air. Further, a bandage comprising the sensor is provided, thereby providing an easily administered method of non-invasively detecting infection in a wound.

BACKGROUND OF THE INVENTION

Despite the best clinical vigilance, secondary exposure to harmful microorganisms can occur in hospital settings, where the routine prescription of antibiotics leads to the development of drug-resistant bacteria. Such exposure to harmful microorganisms commonly result in wound infections and sepsis (infection combined with systemic inflammation), complicating the treatment of many types of diseases and injuries, as well as the management of invasive medical techniques, including surgery, catheterization, and use of mechanical ventilation.

In the United States more than 750,000 cases of sepsis occur each year, resulting in the loss of more than 200,000 lives, making it the $10^{th}$ leading cause of death in the United States. Furthermore, the average cost of sepsis care is approximately $25,000 per episode, and as high as $92,000 per pediatric patient for fungal bloodstream infections. For cancer patients alone, the total cost of treating sepsis has been reported to be $3 billion/year. Overall annual health care costs of sepsis in the United States are estimated to be $16.7 billion. Detection of infection at the earliest possible stage, and intervention with appropriate antibiotic treatment, will greatly reduce mortality and health care costs.

Wound infections have been found to cause production of nitric oxide (NO) in the wound. Accordingly, the detection of wound infections could be accomplished via detection of NO production in and/or adjacent to the wound. However, it has been found that high NO activity sets in soon after the onset of an infection, but that the high (elevated) NO activity persists in the wound only for about 25-30 minutes, after which the levels of NO are drastically reduced again. Therefore, to reliably detect infection in wounds, detection of NO in the wound must be carried out at the onset of infection.

Although not related to wound infection detection, since it is known that NO plays essential roles in mammalian life, there have been attempts to develop sensors for measuring NO in biological systems. The success of these attempts have been hampered by the fact that NO rapidly oxidizes to nitrite and/or nitrate in the presence of oxygen, and that the half life of NO in healthy biological tissues is very short (i.e., ~30 seconds). Different conventional methods for measuring NO in biological systems, and the deficiencies thereof, are shown in Table I below:

TABLE I

Conventional Methods for Measuring NO, and Their Drawbacks

| Technique | In-situ | Non-invasive | Capture and freeze |
| --- | --- | --- | --- |
| Amperometric | No | Yes | No |
| Fluorescence | No | Yes | No |
| Greiss Reaction Assay | No | Yes | No |
| Electrochemical | Yes | No | No |
| Current Proposal | Yes | Yes | Yes |

It has been shown that it is possible to detect a host response (a natural defensive reaction of the body to infection) to early experimentally induced sepsis minutes after the introduction of bacterial components or whole bacteria in a rat (as shown in FIG. 1) and a baboon (as shown in FIG. 2). These measurements were taken using an invasive electrochemical method, wherein the electrode was directly dipped into the wound. However, there are currently no non-invasive methods of measuring the transient amount of NO produced in a wound upon the onset of bacterial infection. Accordingly, it is an object of the present invention to develop a device and method for non-invasively detecting the production of NO in a wound, so as to detect the onset of infection and/or sepsis thereon.

It is a further object of the invention to provide a bandage comprising a non-invasive, calorimetric detector, which can be directly placed above the wound (for example, as part of a bandage), and which will exhibit a persistent change in color when NO activity in the wounds becomes high, so as to alert a user or caregivers of the onset of infection in the wound.

SUMMARY OF THE INVENTION

In order to achieve the objects of the present invention, as discussed above, the present inventors earnestly endeavored to develop a non-invasive, colorimetric infection detector, and bandage comprising same. This detector, when exposed to gaseous oxides of nitrogen and acids formed therefrom, exhibits a color change, indicating to the user the presence of nitric oxide in an underlying wound. When incorporated into a bandage, the present invention provides a convenient, easily applicable, and non-invasive means of detecting the onset of infection and/or sepsis in a wound.

Accordingly, in a first embodiment, a non-invasive, calorimetric infection detector is provided comprising:

(a) a substrate; and (b) an indicator composition capable of sensing gaseous oxides of nitrogen and acids formed therefrom, said indicator composition disposed on, encapsulated within, or covalently linked with the substrate, wherein the detector, when disposed in proximity to a wound, detects gaseous oxides of nitrogen and acids formed therefrom emanating from the wound upon onset of infection therein, and exhibits a color change in response thereto.

In a second embodiment of the present invention, the non-invasive, calorimetric infection detector of the first embodiment above is provided, wherein the color change exhibited by the indicator composition is persistent for 1 or more hours.

In a third embodiment of the present invention, the non-invasive, colorimetric infection detector of the first embodiment is provided, wherein the substrate is a solid, liquid or gel.

In a fourth embodiment of the present invention, the non-invasive, colorimetric infection detector of the third embodiment above is provided, wherein the substrate is a gas permeable hydrophilic substrate.

In a fifth embodiment of the present invention, the non-invasive, colorimetric infection detector of the fourth embodiment above is provided, wherein the gas permeable hydrophilic substrate has a water content of from about 5% to about 95% by weight.

In a sixth embodiment of the present invention, the non-invasive, colorimetric infection detector of the fifth embodiment is provided, wherein the substrate is a gas permeable hydrophilic substrate has a water content of from about 20% to about 95% by weight, said detector further comprising:

(c) a hydrophobic barrier layer disposed adjacent to or attached to the substrate.

In a seventh embodiment of the present invention, the non-invasive, colorimetric infection detector of the third embodiment above is provided, wherein the substrate is a gas impermeable porous solid substrate comprised of one or more of aerogels, xerogels, and zeolites.

In an eighth embodiment of the present invention, the non-invasive, colorimetric infection detector of the third embodiment above is provided, wherein the substrate is comprised of one or more of polyurethane, silicone, nylon, polysulfone, cellulose, alkyl cellulose, cellulose acetate, cellulose xanthate, carboxyalkyl cellulose, hydroxyalkyl cellulose, mineral oil, glycerin, petrolatum, gelatin, polyester, polyolefin, polystyrene, polycarbonate, poly ether ether ketone (PEEK), Teflon®, fluoropolymer, polyacrylamide, polyacrylate, poly(N-vinylpyrrolidone), poly(vinyl alcohol), poly(vinyl acetate), poly(vinyl chloride) (PVC), poly(alkyl oxide), poly(alkylene oxide), poly(methacrylonitrile), poly(lactic acid), poly(maleic acid), poly(lactide/glycolide) copolymer, poly(ethylene glycol)/poly(lactic acid) block polymer, poly[(−)3-hydroxybutryic acid], chitin, chitosan, keratin, alginate, esterified hyaluronans, collagen, maleates, phthalates, adipates, sebacates and citrates.

In a ninth embodiment of the present invention, the non-invasive, colorimetric infection detector of the eighth embodiment above is provided, wherein the indicator composition comprises from between about 0.1 to about 40% by weight of the detector.

In a tenth embodiment of the present invention, the non-invasive, colorimetric infection detector of the first embodiment above is provided, wherein the indicator composition has a pKa in the range of from about 1 to about 6.5.

In an eleventh embodiment of the present invention, the non-invasive, colorimetric infector of the first embodiment above is provided, wherein the indicator composition comprises one or more of phenolsulfonephthaleins, triphenylmethanes, azo dyes, nitrophenols, and styryl dyes.

In a twelfth embodiment of the present invention, the non-invasive, colorimetric infection detector of the eleventh embodiment above is provided, wherein the indicator composition comprises one or more of thymol blue, xylenol blue, m-cresol purple, cresol red, phenol red, methyl violet, methyl green, methyl red, methyl yellow, crystal violet, leuchomalachite green, anilinoazoparabenzene sulfonic acid derivatives, anilinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

In a thirteenth embodiment of the present invention, the non-invasive, colorimetric infection detector of the first embodiment is provided, further comprising an adhesive or elastic attachment means in communication with the substrate, said attachment means operable to attach the sensor to a patient.

In a fourteenth embodiment of the present invention, a non-invasive, calorimetric infection detecting bandage is provided, the bandage comprising:

(a) an indicator substrate;

(b) an indicator composition capable of sensing oxides of nitrogen and acids formed therefrom when disposed on, encapsulated within, or covalently linked to the indicator substrate; and (c) an adhesive portion in communication with the indicator substrate, said adhesive portion capable of adhering the bandage to a patient, wherein, when the bandage is adhered on or in proximity to a wound, the indicator composition detects gaseous oxides of nitrogen and acids formed therefrom emanating from the wound, and exhibits a color change in response thereto so as to detect onset of infection and/or sepsis.

In a fifteenth embodiment of the present invention, the non-invasive, colorimetric infection detecting bandage of the fourteenth embodiment above is provided, wherein the indicator substrate is a cloth or film layer comprised of polymers.

In a sixteenth embodiment of the present invention, the non-invasive, calorimetric infection detecting bandage of the fifteenth embodiment above is provided, wherein the polymers are comprised of one or more of polyurethane, silicone rubber, nylon, polysulfone, cellulose, alkyl cellulose, cellulose acetate, cellulose xanthate, cotton, polyester, polyolefin, silica, gelatin, polystyrene, polycarbonate, poly ether ether ketone (PEEK), Teflon®, fluoropolymer, polyacrylamide, polyacrylate, poly(methacryonitrile), poly(lactic acid), poly(maleic acid), poly(lactide/glycolide) copolymer, poly(ethylene glycol)/poly(lactic acid) block polymer, poly[(−)3-hydroxybutryic acid], keratin, polyvinyl chloride, esterified hyaluronans, latex rubber, polyolefin blends, styrenics, polyolefin/styrenic blends, metallocene polymers, acrylonitrile butadiene styrene (ABS), styrene butadiene styrene (SBS), fluoroelastomers, polyisoprene, and polychloroprene, maleates, phthalates, adipates, sebacates and citrates.

In a seventeenth embodiment of the present invention, the non-invasive, colorimetric infection detecting bandage of the fourteenth embodiment above is provided, wherein the indicator composition has a pKa in the range of from about 1 to about 6.5.

In an eighteenth embodiment of the present invention, the non-invasive, colorimetric infection detecting bandage of the fourteenth embodiment above is provided, wherein the indicator composition is comprised of one or more of phenolsulfonephthaleins, triphenylmethanes, azo dyes, nitrophenols, and styryl dyes.

In a nineteenth embodiment of the present invention, the non-invasive, colorimetric infection detecting bandage of the fourteenth embodiment above is provided, wherein the indicator composition is comprised of one or more of thymol blue, xylenol blue, m-cresol purple, cresol red, phenol red, methyl violet, methyl green, methyl red, methyl yellow, crystal violet, leuchomalachite green, anilinoazoparabenzene sulfonic acid derivatives, anilinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

In a twentieth embodiment of the present invention, the non-invasive, colorimetric infection detecting bandage of the fourteenth embodiment above is provided, further comprising a hydrophobic barrier layer disposed adjacent the indicator substrate, so as to face the wound and prevent absorption of fluids into the indicator substrate.

In a twenty first embodiment of the present invention, the non-invasive, calorimetric infection detecting bandage of the twentieth embodiment above is provided, wherein the hydrophobic barrier layer is comprised of one or more of latex rubber, silicone rubber, polyolefin blends, styrenics, polyolefin/styrenic blends, nylons, polyurethanes, metallocene polymers, acrylonitrile butadiene styrene (ABS), styrene butadiene styrene (SBS), polyvinyl chloride (PVC), fluoroelastomers, polyisoprene, and polychloroprene.

In a twenty second embodiment of the present invention, an infection detecting bandage is provided, the bandage comprising:

(a) a porous portion which can be positioned on or adjacent a wound, said porous portion comprising a non-invasive colorimetric indicator composition which, when disposed in proximity to a wound, detects gaseous oxides of nitrogen and acids formed therefrom emanating from the wound upon onset of infection therein, and exhibits a color change in response thereto; and (b) an adhesive or elastic portion attached to the porous portion, operable to adhere or dispose the bandage to an area of the wound.

In a twenty third embodiment of the present invention, the infection detecting bandage of the twenty second embodiment above is provided, wherein the porous portion is a cloth or film comprised of one or more of polyurethane, silicone rubber, nylon, polysulfone, cellulose, alkyl cellulose, cellulose acetate, cellulose xanthate, carboxyalkyl cellulose, hydroxyalkyl cellulose, cotton, polyester, polyolefin, silica, polystyrene, polycarbonate, poly ether ether ketone (PEEK), Teflon®, fluoropolymer, polyacrylamide, polyacrylate, poly (N-vinylpyrrolidone), poly(vinyl alcohol), poly(vinyl acetate), poly(alkyl oxide), poly(alkylene oxide), poly(methacryonitrile), poly(lactic acid), poly(maleic acid), poly(lactide/glycolide) copolymer, poly(ethylene glycol)/poly(lactic acid) block polymer, poly[(−)3-hydroxybutryic acid], gelatin, chitin, chitosan, keratin, alginate, esterified hyaluronans, collagen, PVC, esterified hyaluronans, latex rubber, polyolefin blends, styrenics, polyolefin/styrenic blends, metallocene polymers, acrylonitrile butadiene styrene (ABS), styrene butadiene styrene (SBS), fluoroelastomers, polyisoprene, and polychloroprene, mineral oil, petrolatum, with or without plasticizer, plasticizer classes including maleates, phthalates, adipates, sebacates and citrates.

In a twenty fourth embodiment of the present invention, the infection detecting bandage of the twenty second embodiment above is provided, wherein the color change exhibited by the indicator composition is persistent for 1 or more hours.

In a twenty fifth embodiment of the present invention, the infection detecting bandage of the twenty second embodiment above is provided, wherein the indicator composition has a pKa in the range of from about 1 to about 6.5.

In a twenty sixth embodiment of the present invention, the infection detecting bandage of the twenty second embodiment above is provided, wherein the indicator composition is one or more of phenolsulfonephthaleins, triphenylmethanes, azo dyes, nitrophenols, and styryl dyes.

In a twenty seventh embodiment of the present invention, the infection detecting bandage of the twenty sixth embodiment above is provided, wherein the indicator composition is one or more selected from the group consisting of thymol blue, xylenol blue, m-cresol purple, phenol red, cresol red, methyl violet, methyl green, methyl red, methyl yellow, crystal violet, leuchomalachite green, anilinoazoparabenzene sulfonic acid derivatives, anilinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

In a twenty eighth embodiment of the present invention, the infection detecting bandage of the twenty second embodiment above is provided, wherein the adhesive or elastic portion is comprised of one or more of polyacrylate, polymethacrylate, polyurethane, silicone, hydrogel, hydrocolloid, rosin, terpene, polyvinyl acrylate, gum Arabic, latex, starch, mucilage, hydrolyzed keratin, casein, albumin, metallocene polymers, polychloroprene, cellulose, polyvinyl acetate.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

As mentioned above, and as illustrated in FIGS. 1 and 2, NO (nitric oxide) activity increases by a factor of 1000 soon after infection sets in the wound. However, the high NO activity is a "transient" phenomenon (i.e., it lasts only about 30 minutes or less). It should be noted that the responses shown in FIGS. 1 and 2 were authentic nitric oxide signals, and were corroborated by the fact that they could be abolished when an inhibitor of nitric oxide synthesis, $N^G$-nitro-L-arginine methyl ester (L-NAME), was administered 30 minutes prior to the introduction of the infectious agent. In addition, in vitro studies have shown that the measuring sensor used in these studies is highly specific for nitric oxide, and relatively insensitive to substances that would likely be present in biological systems which could produce a signal at the electrode, and thus be confounded (mistaken) with nitric oxide.

Figure 1:
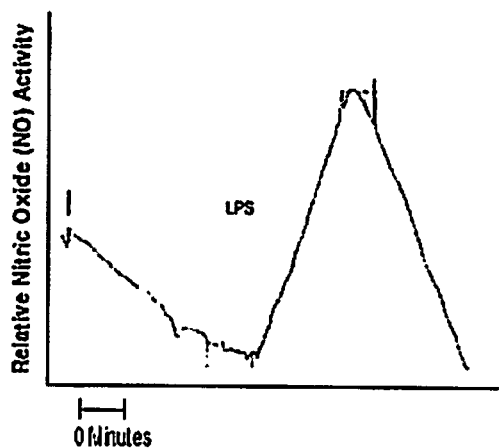
FIG. 1 is a graph illustrating measurements of nitric oxide signals, after lipopolysaccharide (LPS, 1 mg/kg) was injected into the peritoneal cavity of an anesthetized rat, taken using an invasive electrochemical method, wherein the electrode was directly dipped into the wound, eliciting a strong signal at an NO-selective electrode in the vena cava.

For example, various tests have been carried out to determine whether NO activity (production) increases in the wound upon onset of infection therein. In one test, lipopolysaccharide (LPS, 1 mg/kg) was injected into the peritoneal cavity of an anesthetized rat, and the NO-activity therein measured thereafter using an invasive electrochemical method (wherein the electrode was directly dipped into the wound). As shown in FIG. 1, a strong signal, indicating NO activity (production), was measured by the electrode in the vena cava by an NO-selective electrode in the vena cava.

In a further test, carried out to determine the pathological levels of NO in vivo upon infection, an intravascular nitric oxide sensor (comprising a ruthenium electrode) was inserted into a femoral vein in an anesthetized baboon (*Papio cynocephius*), according to an approved protocol. Then, heat-killed bacteria (*E. coli*) were infused into a brachial vein (arrow). Approximately 20 minutes later, the output of the ruthenium electrode demonstrated a strong signal consistent with nitric oxide production by the animal in response to the experimental bacteremia, as illustrated in the graph shown in FIG. 2.

Based on these tests, it is believed that any method and/or device capable of reliably measuring NO production in wounds, so as to detect the onset of infection therein, preferably has seven important attributes as follows:

1) It must be an in-situ technique. Analytical methods that are essentially laboratory techniques are not suitable;

2) It should be non-invasive, thus minimizing the chances of additional infections;

3) It must be able to capture and freeze the information on NO activity without a medical attendant being present in the short transient time in which the NO activity is at its maximum;

4) It should be sensitive enough to detect gaseous oxides of nitrogen and acids formed therefrom (gas emanating from the wound) diffusing through a porous bandage;

5) It should respond selectively to gaseous oxides of nitrogen and acids formed therefrom;

6) It should have sufficiently low level detection capability (as test data indicates that the NO levels range from picomolar to nanomolar concentrations (a 1000-fold increase) within a 25-30 minute time frame); and 7) The color change must be persistent for a reasonable time, so as to ensure detection by a user or caregiver even after the rise in NO denoting the first sign of infection subsides.

Accordingly, the present inventors have determined that a device that detects gaseous oxides of nitrogen and acids formed therefrom may be used to detect the formation of nitric oxide in the wound, and thereby, infection and/or sepsis in the wound. In particular, the generation of nitric acid from nitric oxide occurs by a step-wise set of reactions, including the generation of nitrous acid, which readily decomposes to form small quantities of nitric acid according to the following equation:

$$4NO + 2H_2O + O_2 \rightarrow 4HNO_2 \rightarrow 2HNO_3 + H_2O + N_2O$$

Taking into account the above considerations, the present inventors have found that detecting the presence of gaseous oxides of nitrogen and acids formed therefrom, especially nitric acid, is readily accomplished using various indicator compositions, such as phenolsulfonephthaleins, triphenylmethanes, azo dyes, nitrophenols, and styryl dyes, which exhibit protonation of their phenolic groups in a preferred pH range. This protonation occurs without needing to use an indicator-quaternary ion pair, making the indicator compositions more likely to survive the extreme temperatures and conditions required for the extrusion of the thin films incorporating same used in the construction of detectors, bandages, wound dressings, etc.

Figures 4A, 4B, 4C:
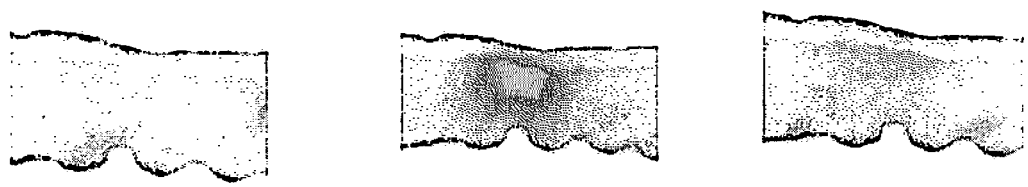
FIG. 4(a) is a photograph of a top view of the non-invasive, calorimetric infection detector of the present invention, before exposure of same to $HNO_3$ vapor.
FIG. 4(b) is a photograph of a top view of the non-invasive, colorimetric infection detector of the present invention shown in FIG. 4(b), illustrating the color change therein immediately after exposure of same to $HNO_3$ vapor.
FIG. 4(c) is a photograph of a top view of the non-invasive, colorimetric infection detector of the present invention shown in FIG. 4(c), illustrating the color of same 3 hours after exposure of same to $HNO_3$ vapor, and removal of the film from the presence of the vapor.
Figure 5:
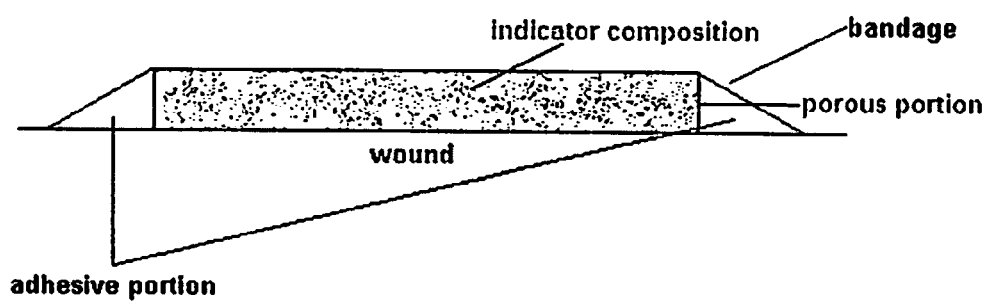
FIG. 5 is a cross sectional view of another embodiment of the non-invasive colorimetric-based infection detection bandage of the present invention.

The present inventors carried out numerous tests to determine the effectiveness and reliability of such indicator compositions. The results of one set of such tests is illustrated in FIGS. 4(a)-4(c), illustrating a non-invasive, calorimetric infection detector of the present invention comprised of 4% by weight Thymol Blue (indicator composition) in HydroMed® D640 (a hydrophilic medical grade polyurethane, acting as the substrate). When this detector was exposed to gaseous oxides of nitrogen and acids formed therefrom, there was exhibited a persistent color change in response thereto.

Another unique challenge to overcome in developing the present invention was that all known conventional aqueous-based conventional calorimetric pH indicators exhibit rapid, reversible color changes. However, such a characteristic would not allow a sufficient window of time to a user of the present invention for detection of infection and/or sepsis (as such a rapid, reversible color change would require constant monitoring). Rather, it is desirable to have the color change be persistent for a time sufficient for a user to periodically view same. Accordingly, the present inventors found that only certain indicator compositions exhibit a color change that is persistent for 1 or more hours, so as to enable caregivers and patients to easily monitor the status of infection.

This function is possible by use of an indicator composition that is deployed as a free acid, with sufficiently low pKa so as to eliminate the potential for cross reactivity with other naturally occurring volatile acids or acid-forming gases, such as acetic acid and $CO_2$. Further, the present inventors have unexpectedly discovered that the production of nitric oxide (NO) by activated inflammatory cells is a sentinel event common to the early stages of all infections which elicit an immune response. This response includes, but is not limited to, bacterial, viral or fungal infection. Thus, infection by all types of foreign bodies may be detected via detection of NO production.

Accordingly, in a first embodiment of the present invention, a non-invasive, colorimetric infection detector is provided. This detector is comprised of a substrate, and an indicator composition disposed on, encapsulated within, or covalently linked with the substrate. The substrate may be a solid, liquid or gel. However, regardless of the form of substrate chosen, it is important that gases emanating from the wound may reach the indicator composition disposed on, encapsulated within, or covalently linked with the substrate.

In a preferred embodiment, the substrate is a gas permeable hydrophilic substrate. For example, the substrate may be comprised of one or more of polyurethane, silicone, nylon, polysulfone, cellulose, alkyl cellulose, cellulose acetate, cellulose xanthate, carboxyalkyl cellulose, hydroxyalkyl cellulose, mineral oil, petrolatum, gelatin, polyester, polyolefin, polystyrene, polycarbonate, poly ether ether ketone (PEEK), Teflon®, fluoropolymer, polyacrylamide, polyacrylate, poly (N-vinylpyrrolidone), poly(vinyl alcohol), poly(vinyl acetate), poly(vinyl chloride) (PVC), poly(alkyl oxide), poly (alkylene oxide), poly(methacryonitrile), poly(lactic acid), poly(maleic acid), poly(lactide/glycolide) copolymer, poly (ethylene glycol)/poly(lactic acid) block polymer, poly[(−)3-hydroxybutryic acid], chitin, chitosan, keratin, alginate, esterified hyaluronans, collagen, maleates, phthalates, adipates, sebacates and citrates.

In a further preferred embodiment, the substrate is comprised of a gas impermeable porous solid substrate. Examples of such gas impermeable porous solid substrates include aerogels, xerogels, and zeolites. These solid types of porous, solid substrates allow the indicator composition to be easily deposited thereon, while the porosity allows gaseous nitrogen compounds to come into direct contact with the indicator composition.

In yet a further preferred embodiment, the substrate is a gas permeable hydrophilic substrate having a water content of from about 5% to about 95% by weight, more preferably from about 20% to about 95% by weight. When, the substrate of the detector has a water content of 20% or greater, the detector preferably comprises a hydrophobic barrier layer, disposed adjacent to or attached to the substrate, to prevent absorption of bulk water into the detector. Such a hydrophobic barrier layer is preferably disposed so as to face the wound, and prevent absorption of fluids into the indicator substrate. In a preferred embodiment, the hydrophobic barrier layer is comprised of one or more of latex rubber, silicone rubber, polyolefin blends, styrenics, polyolefin/styrenic blends, nylons, polyurethanes, metallocene polymers, acrylonitrile butadiene styrene (ABS), styrene butadiene styrene (SBS), polyvinyl chloride (PVC), fluoroelastomers, polyisoprene, and polychloroprene.

In a further preferred embodiment, the polymer substrate is coated with a layer of adhesive, such as an acrylic emulsion adhesive, so as to bond the polymer substrate to the hydrophobic barrier layer. For example, OPSITE IV 3000®, a commercially available wound dressing, which consists of a thin hydrophilic polyurethane membrane coated with a layer of an acrylic emulsion adhesive, may be utilized as the hydrophobic barrier layer. Because of the hydrophilic nature of the film, the dressing is highly permeable to water vapour, (about 3000 $g/m^2/24$ hours), but impermeable to micro-organisms. Once in position, therefore, it provides an effective barrier to bulk water and external contamination.

As mentioned above, the indicator composition is provided to detect the presence of gaseous oxides of nitrogen and acids formed therefrom. In terms of manufacturing considerations, the indicator composition should be chosen based on the stability of the doped indicator to normal processing conditions, including thin-film extrusion, adhesive deposition and sterilization. Generally, the indicator composition comprises from between about 0.1 wt % to about 40% wt % of the detector. Further, the indicator composition has a pKa in the range of from about 1 to about 6.5. Maintaining the pKa within this range is important, as this pKa range is too low for protonation by either acetic or carbonic acid, which could interfere with the detection method of the present invention (i.e., the detection of nitric acid). This range of pKa further provides stability, i.e., a persistent color change. Preferably, the indicator composition exhibits a color change that is persistent for at least one hour, which provides sufficient time to patients and caregivers to observe the color change without constant monitoring.

The indicator compositions are comprised, generally, of one or more of phenolsulfonephthaleins, triphenylmethanes, azo dyes, nitrophenols, and styryl dyes. In a preferred embodiment, the indicator composition is comprised of one or more of thymol blue, xylenol blue, m-cresol purple, cresol red, phenol red, methyl violet, methyl green, methyl red, methyl yellow, crystal violet, leuchomalachite green, anilinoazoparabenzene sulfonic acid derivatives, anilinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

Figure 3:
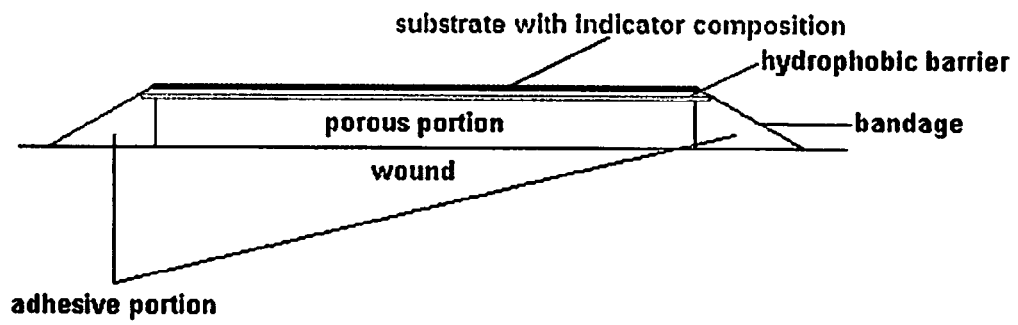
FIG. 3 is a cross sectional view of a non-invasive colorimetric-based infection detection bandage of the present invention.

In a further embodiment, as shown in FIG. 3, and as called for in the fourteenth embodiment described above, the non-invasive, calorimetric infection detector of the present invention may be incorporated into a bandage, so as to provide a convenient means of application/use by patients and/or caregivers. In particular, the present invention provides a non-invasive, calorimetric infection detecting bandage, wherein the bandage comprises an indicator substrate, an indicator composition disposed on, encapsulated within, or covalently linked to the indicator substrate, and an adhesive portion. The substrate and indicator composition of the bandage may be the same substrates and indicators as described in the detector embodiment described above.

However, unlike the detector described above, the adhesive portion of the bandage is capable of adhering the bandage to a patient. This allows the indicator composition on the substrate to be adhered on or in proximity to a wound. Accordingly, when the indicator composition detects gaseous oxides of nitrogen and acids formed therefrom emanating from the wound, the indicator composition exhibits a persistent color change in response thereto, alerting a caregiver or patient to the onset of infection and/or sepsis. Thus, the bandage application of the present invention provides a convenient means of use in the field.

In the bandage application described above, in a preferred embodiment, the indicator substrate is a cloth, such as cotton cloth or gauze, or a film layer comprised of polymers. In a further preferred embodiment, the indicator substrate is a polymer comprised of one or more of polyurethane, silicone rubber, nylon, polysulfone, cellulose, alkyl cellulose, cellulose acetate, cellulose xanthate, cotton, polyester, polyolefin, silica, gelatin, polystyrene, polycarbonate, poly ether ether ketone (PEEK), Teflon®, fluoropolymer, polyacrylamide, polyacrylate, poly(methacryonitrile), poly(lactic acid), poly(maleic acid), poly(lactide/glycolide) copolymer, poly(ethylene glycol)/poly(lactic acid) block polymer, poly[(−)3-hydroxybutryic acid], keratin, polyvinyl chloride, esterified hyaluronans, latex rubber, polyolefin blends, styrenics, polyolefin/styrenic blends, metallocene polymers, acrylonitrile butadiene styrene (ABS), styrene butadiene styrene (SBS), fluoroelastomers, polyisoprene, and polychloroprene, maleates, phthalates, adipates, sebacates and citrates.

In a further embodiment of the present invention, an infection detecting bandage is provided, comprising a porous portion which can be positioned on or adjacent a wound. The porous portion comprises the indicator composition as described above. Further, an adhesive or elastic portion is attached to the porous portion, allowing the bandage to be adhered to or disposed adjacent the area of a wound. Like the substrate of the non-invasive, colorimetric infection detector, the porous portion of the infection detecting bandage is a cloth or film.

In a preferred embodiment, the porous portion is comprised of one or more of polyurethane, silicone rubber, nylon, polysulfone, cellulose, alkyl cellulose, cellulose acetate, cellulose xanthate, carboxyalkyl cellulose, hydroxyalkyl cellulose, cotton, polyester, polyolefin, silica, polystyrene, polycarbonate, poly ether ether ketone (PEEK), Teflon®, fluoropolymer, polyacrylamide, polyacrylate, poly(N-vinylpyrrolidone), poly(vinyl alcohol), poly(vinyl acetate), poly(alkyl oxide), poly(alkylene oxide), poly(methacryonitrile), poly(lactic acid), poly(maleic acid), poly(lactide/glycolide) copolymer, poly(ethylene glycol)/poly(lactic acid)

block polymer, poly[(−)3-hydroxybutryic acid], gelatin, chitin, chitosan, keratin, alginate, esterified hyaluronans, collagen, PVC, esterified hyaluronans, latex rubber, polyolefin blends, styrenics, polyolefin/styrenic blends, metallocene polymers, acrylonitrile butadiene styrene (ABS), styrene butadiene styrene (SBS), fluoroelastomers, polyisoprene, and polychloroprene, mineral oil, petrolatum, with or without plasticizer, plasticizer classes including maleates, phthalates, adipates, sebacates and citrates.

Figure 2:
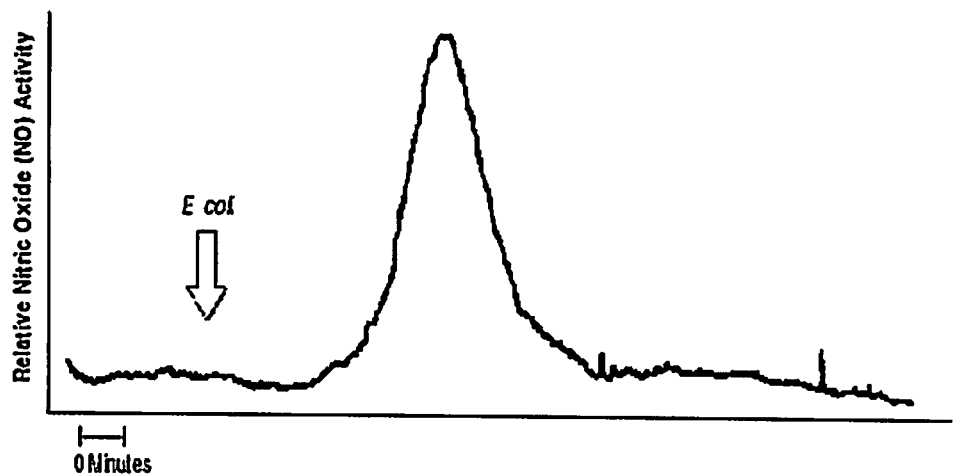
FIG. 2 is a graph of relative nitric oxide activity in a wound over time, after exposure of the wound to bacterial infection.

In a further preferred embodiment, the low pKa pH indicator composition is incorporated directly into a highly gas permeable hydrophilic polyurethane of the type that is used to form the hydrophobic barrier layer of commercially available wound dressings. In such a structure, NO generated at the wound site is free to diffuse into the gas permeable dressing, where the NO can react with water and oxygen so as to form nitric acid. Considering that the high NO activity exhibited early in the infection process is transient in nature (as illustrated in FIGS. 1 and 2), the color change of the detector is designed to be persistent, i.e., at least in the time scale of an hour or more.

Therefore, a medical attendant, or even the patient himself, can be forewarned of the impending infection without the need for continuous monitoring of the detector disposed on the bandage. The irreversible nature of the reaction between nitric acid and the indicator also aids in the limit of detection possible by enabling the detector to function with a cumulative response.

Another important element of the detector design is availability of water and oxygen within the detector, which, as illustrated in the reaction formula shown above, facilitates the formation and decomposition of nitrous oxide from nitric oxide. This requirement may be satisfied by, instead of coating the sensing indicator composition on the polymer substrate, deploying the indicator composition within the gas permeable polymer substrate (such as a hydrophilic polyurethane). However, disposition of the sensing indicator composition within the gas permeable polymer substrate presents further manufacturing difficulties, namely, the indicator composition must exhibit a high level of stability under normal processing conditions (e.g., extrusion) required to form the thin films used in wound dressings.

Accordingly, preferred indicator compositions have the following characteristics:

(1) The indicator compositions may be utilized in conventional extrusion manufacturing processes.

(2) The indicator compositions maintain, or experience only a minimal degradation, in their response to nitric acid vapors after being incorporated into the polymer membrane.

(3) The indicator compositions are stable over the time scale of the proposed application.

(4) The persistent color change exhibited by the indicator compositions is of the greatest possible magnitude in the presence of a minimum amount of nitrous oxide.

(5) The indicator composition should be sensitive enough to detect nanomolar concentrations of NO. This will enable the detection of NO activity at the early stage of infection.

(6) The indicator composition should work in high oxygen environment and excess water vapor. This will ensure that the infection detector can work in an atmospheric oxygen environment and in presence of humidity in the environment.

(7) The indicator compositions should be able to withstand temperatures of about 200° C. or higher. This will assure that we will be able to incorporate the sensor into a conventional polyurethane-type dressing.

PREPARATION EXAMPLES:

Example 1

HydroMed® D640 (by AdvanSource® biomaterials), a hydrophilic medical grade polyurethane, was dissolved in 95/5 absolute ethanol/DI water, so as to make a 2.5 wt. % polymer solution thereof. Then, Thymol Blue (the acid form of thymolsulphonephthalein), an indicator, was incorporated into the polymer solution in a sufficient amount so as to yield a 4 wt. % indicator/polymer solution. This polymer solution was then cast onto a glass plate, and the solvent allowed to evaporate, thereby providing a non-invasive, calorimetric infection detector.

Example 2

Methyl Yellow (acid form), a pH indicatior, was dissolved in methanol, so as to yield a 1 mg/mL solution thereof. Then, a ~1 $cm^2$ piece of 20 micron pore size nylon (produced by GE Osmonics®) was soaked in the Methyl Yellow solution for one minute. The solvent was then allowed to evaporate, thereby providing a non-invasive, calorimetric infection detector.

Example 3

HydroThane® 25-93A (by AdvanSource® biomaterials), a thermoplastic hydrogel, was dissolved in N,N'-dimethylacetamide, so as to make a polymer solution having 2.5% by weight of solids therein. Then, Thymol Blue (thymolsulphonephthalein, acid form), an indicator composition, was dissolved in the polymer solution, so as to yield a 4 wt. % indicator/polymer composition. The indicator/polymer solution was then added dropwise to a beaker of water. The resultant precipitate was collected for extrusion. This precipitate was then dried, compacted, and extruded, so as to provide a non-invasive, calorimetric infection detector.

Example 4

Methyl Red, a pH indicator, was dissolved in methanol, so as to yield a 1 mg/mL indicator solution. A ~1 $cm^2$ piece of 20 micron pore size polysulfone (producted by GE Osmonics®) was then soaked in said indicator solution for one minute. The solvent was then allowed to evaporate, thereby leaving a non-invasive, calorimetric infection detector.

Example 5

Methyl Red, a pH indicator, was dissolved in methanol so as to yield a 1 mg/mL indicator solution. Several drops of said indicator solution were then dispersed onto the surface of a Smith & Nephew® Opsite® IV3000 wound dressing. The solvent was allowed to evaporate, thereby providing an infection detecting bandage.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. A non-invasive, colorimetric infection detector comprising:
   (a) a substrate; and
   (b) an indicator composition capable of sensing gaseous oxides of nitrogen and acids formed therefrom, said indicator composition disposed on, encapsulated within, or covalently linked with the substrate; wherein the indicator composition has a pKa in the range of from greater than 1 to about 6.5;
   wherein the indicator composition comprises one or more of phenolsulfonephthaleins, triphenylmethanes, azo dyes, nitrophenols, and styryl dyes; and
   wherein the detector, when disposed in proximity to a wound, detects gaseous oxides of nitrogen and acids formed therefrom emanating from the wound upon onset of infection therein, and exhibits a color change in response thereto.

2. The non-invasive, colorimetric infection detector of claim 1, wherein the color change exhibited by the indicator composition is persistent for 1 or more hours.

3. The non-invasive, colorimetric infection detector of claim 1, wherein the substrate is a solid, liquid or gel.

4. The non-invasive, colorimetric infection detector of claim 3, wherein the substrate is a gas permeable hydrophilic substrate.

5. The non-invasive, colorimetric infection detector of claim 4, wherein the gas permeable hydrophilic substrate has a water content of from about 5% to about 95% by weight.

6. The non-invasive, colorimetric infection detector of claim 5, wherein the substrate is a gas permeable hydrophilic substrate has a water content of from about 20% to about 95% by weight, said detector further comprising:
   (c) a hydrophobic barrier layer disposed adjacent to or attached to the substrate.

7. The non-invasive, colorimetric infection detector of claim 3, wherein the substrate is a gas impermeable porous solid substrate comprised of one or more of aerogels, xerogels, and zeolites.

8. The non-invasive, colorimetric infection detector of claim 3, wherein the substrate is comprised of one or more of polyurethane, silicone, nylon, polysulfone, cellulose, alkyl cellulose, cellulose acetate, cellulose xanthate, carboxyalkyl cellulose, hydroxyalkyl cellulose, mineral oil, glycerin, petrolatum, gelatin, polyester, polyolefin, polystyrene, polycarbonate, poly ether ether ketone (PEEK), Teflon®, fluoropolymer, polyacrylamide, polyacrylate, poly(N-vinylpyrrolidone), poly(vinyl alcohol), poly(vinyl acetate), poly(vinyl chloride) (PVC), poly(alkyl oxide), poly(alkylene oxide), poly(methacrylonitrile), poly(lactic acid), poly(maleic acid), poly(lactide/glycolide) copolymer, poly(ethylene glycol)/poly(lactic acid) block polymer, poly[(−)3-hydroxybutryic acid], chitin, chitosan, keratin, alginate, esterified hyaluronans, collagen, maleates, phthalates, adipates, sebacates and citrates.

9. The non-invasive, colorimetric infection detector of claim 8, wherein the indicator composition comprises from between about 0.1 to about 40% by weight of the detector.

10. The non-invasive, colorimetric infection detector of claim 1, wherein the indicator composition comprises one or more of thymol blue, xylenol blue, m-cresol purple, cresol red, methyl violet, methyl green, methyl red, methyl yellow, leuchomalachite green, aniliinoazoparabenzene sulfonic acid derivatives, anillinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

11. The non-invasive, colorimetric infection detector of claim 1, further comprising an adhesive or elastic attachment means in communication with the substrate, said attachment means operable to attach the sensor to a patient.

12. A non-invasive, colorimetric infection detecting bandage comprising:
   (a) an indicator substrate;
   (b) an indicator composition capable of sensing oxides of nitrogen and acids formed therefrom when disposed on, encapsulated within, or covalently linked to the indicator substrate; wherein the indicator composition has a pKa in the range of from greater than 1 to about 6.5; and wherein the indicator composition comprises one or more of phenolsulfonephthaleins, triphenylmethanes, azo dyes, nitrophenols, and styryl dyes; and
   (c) an adhesive portion in communication with the indicator substrate, said adhesive portion capable of adhering the bandage to a patient,
   wherein, when the bandage is adhered on or in proximity to a wound, the indicator composition detects gaseous oxides of nitrogen and acids formed therefrom emanating from the wound, and exhibits a color change in response thereto so as to detect onset of infection and/or sepsis.

13. The non-invasive, colorimetric infection detecting bandage of claim 12, wherein the indicator substrate is a cloth or film layer comprised of polymers.

14. The non-invasive, colorimetric infection detecting bandage of claim 13, wherein the polymers are comprised of one or more of polyurethane, silicone rubber, nylon, polysulfone, cellulose, alkyl cellulose, cellulose acetate, cellulose xanthate, cotton, polyester, polyolefin, silica, gelatin, polystyrene, polycarbonate, poly ether ether ketone (PEEK), Teflon®, fluoropolymer, polyacrylamide, polyacrylate, poly(methacryonitrile), poly (lactic acid), poly(maleic acid), poly(lactide/glycolide) copolymer, polyethylene glycol)/poly (lactic acid) block polymer, poly[(−)3-hydroxybutryic acid], keratin, polyvinyl chloride, esterified hyaluronans, latex rubber, polyolefin blends, styrenics, polyolefin/styrenic blends, metallocene polymers, acrylonitrile butadiene styrene (ABS), styrene butadiene styrene (SBS), fluoroelastomers, polyisoprene, and polychloroprene, maleates, phthalates, adipates, sebacates and citrates.

15. The non-invasive, colorimetric infection detecting bandage of claim 12, wherein the indicator composition is comprised of one or more of thymol blue, xylenol blue, m-cresol purple, cresol red, methyl violet, methyl green, methyl red, methyl yellow, leuchomalachite green, anilinoazoparabenzene sulfonic acid derivatives, anilinoazobenzene derivatives, anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

16. The non-invasive, colorimetric infection detecting bandage of claim 12, further comprising a hydrophobic barrier layer disposed adjacent the indicator substrate, so as to face the wound and prevent absorption of fluids into the indicator substrate.

17. The non-invasive, colorimetric infection detecting bandage of claim 16, wherein the hydrophobic barrier layer is comprised of one or more of latex rubber, silicone rubber, polyolefin blends, styrenics, polyolefin/styrenic blends, nylons, polyurethanes, metallocene polymers, acrylonitrile butadiene styrene (ABS), styrene butadiene styrene (SBS), polyvinyl chloride (PVC), fluoroelastomers, polyisoprene, and polychloroprene.

18. An infection detecting bandage comprising:
(a) a porous portion which can be positioned on or adjacent a wound, said porous portion comprising a non-invasive colorimetric indicator composition which, when disposed in proximity to a wound, detects gaseous oxides of nitrogen and acids formed therefrom emanating from the wound upon onset of infection therein, and exhibits a color change in response thereto; wherein the indicator composition comprises one or more of phenolsulfonephthaleins, triphenylmethanes, azo dyes, nitrophenols, and styryl dyes; and
wherein the indicator composition has a pKa in the range of from greater than 1 to about 6.5; and
(b) an adhesive or elastic portion attached to the porous portion, operable to adhere or dispose the bandage to an area of the wound.

19. The infection detecting bandage of claim 18, wherein the porous portion is a cloth or film comprised of one or more of polyurethane, silicone rubber, nylon, polysulfone, cellulose, alkyl cellulose, cellulose acetate, cellulose xanthate, carboxyalkyl cellulose, hydroxyalkyl cellulose, cotton, polyester, polyolefin, silica, polystyrene, polycarbonate, poly ether ether ketone (PEEK), Teflon ®fluoropolymer, polyacrylamide, polyacrylate, poly(N-vinylpyrrolidone), poly(vinyl alcohol), poly(vinyl acetate), poly(alkyl oxide), poly(alkylene oxide), poly(methacrylonitrile), poly(lactic acid), poly(maleic acid), poly(lactide/glycolide) copolymer, poly(ethylene glycol)/poly(lactic acid) block polymer, poly[(−)3-hydroxybutryic acid], gelatin, chitin, chitosan, keratin, alginate, esterified hyaluronans, collagen, PVC, esterified hyaluronans, latex rubber, polyolefin blends, styrenics, polyolefin/styrenic blends, metallocene polymers, acrylonitrile butadiene styrene (ABS), styrene butadiene styrene (SBS), fluomelastomers, polyisoprene, and polychloroprene, mineral oil, glycerin, petrolatum, maleates, phthalates, adipates, sebacates and citrates.

20. The infection detecting bandage of claim 18, wherein the color change exhibited by the indicator composition is persistent for 1 or more hours.

21. The infection detecting bandage of claim 18 wherein the indicator composition is one or more selected from the group consisting of thymol blue, xylenol blue, m-cresol purple, cresol red, methyl violet, methyl green, methyl red, methyl yellow, leuchomalachite green, and anilinooazoparabenzene sulfonic acid derivatives, anilinoazobenzene derivatives, and anilinoazoparatoluene derivatives, α-naphthylaminoazoparabenzene sulfonic acid derivatives, α-naphthylaminoazobenzene derivatives, α-naphthylaminoazotoluene derivatives, 2,4-dinitrophenol and 2,5-dinitrophenol, quinaldine red (2-(4-dimethylaminostyryl)-ethylquinolinium iodide) and p-ethoxy quinaldine-p-ethoxy quinoline.

22. The infection detecting bandage of claim 18, wherein the adhesive or elastic portion is comprised of one or more of polyacrylate, polymethacrylate, polyurethane, silicone, hydrogel, hydrocolloid, rosin, terpene, polyvinyl acrylate, polyvinyl alcohol, gum Arabic, latex, starch, mucilage, hydrolyzed keratin, casein, albumin, metallocene polymers, polychloroprene, cellulose, polyvinyl acetate.

* * * * *

UNITED STATES PATENT AND TRADEMARK OFFICE
CERTIFICATE OF CORRECTION

PATENT NO.        : 8,628,728 B2
APPLICATION NO.   : 12/354708
DATED             : January 14, 2014
INVENTOR(S)       : James A. Kane et al.

It is certified that error appears in the above-identified patent and that said Letters Patent is hereby corrected as shown below:

In the Claims

In column 13, line 47 (claim 8), "polyacry late" should read --polyacrylate--

In column 15, line 29 (claim 19), "Teflon ®fluoropolymer," should read --Teflon® fluoropolymer--

In column 16, line 6 (claim 19), "fluormelastomers," should read --fluoromelastomers--

Signed and Sealed this
Twenty-second Day of April, 2014

Michelle K. Lee
*Deputy Director of the United States Patent and Trademark Office*